United States Patent [19] [11] 4,428,887
Tou et al. [45] Jan. 31, 1984

[54] METHOD OF PRODUCING MONO-SUBSTITUTED TERMINAL DIESTERS

[75] Inventors: Jacob S. Tou; Alfred A. Schleppnik, both of St. Louis, Mo.

[73] Assignee: Monsanto Company, St. Louis, Mo.

[21] Appl. No.: 398,060

[22] Filed: Jul. 14, 1982

[51] Int. Cl.³ .................... C07C 120/00; C07C 67/34
[52] U.S. Cl. ............................ 260/465 D; 260/465.4; 560/81; 560/190; 560/203
[58] Field of Search ................ 560/190, 193, 203, 81; 260/465 D, 465.4

[56] References Cited

U.S. PATENT DOCUMENTS

| | | | |
|---|---|---|---|
| 1,869,666 | 8/1932 | Chaux et al. | 544/304 |
| 1,954,429 | 4/1934 | Shonle | 544/306 |
| 2,153,730 | 4/1939 | Volwiler et al. | 544/305 X |
| 2,872,448 | 2/1959 | Doran | 544/306 |
| 2,876,225 | 3/1959 | Donnison | 260/257 |

FOREIGN PATENT DOCUMENTS 146496 7/1902 Fed. Rep. of Germany .
1059M 1/1962 France .
940533 10/1963 United Kingdom .

OTHER PUBLICATIONS

C. A. Bischoff, *Ber.* 29 (1), 966–967, (1896).
D. A. White, S. *Synthetic Comm.* 7 (8), 559–568, (1977).
Holden and Lapworth, *J. Chem. Soc.*, 2368–2373, (1931).

*Primary Examiner*—Natalie Trousof
*Assistant Examiner*—Vera C. Clarke
*Attorney, Agent, or Firm*—Scott J. Meyer; James W. Williams, Jr,

[57] ABSTRACT

Mono-substituted terminal diesters of malonic acid are prepared by reaction of the corresponding substituted 1,2-diesters with alkali metal hydride in the presence of organic solvent medium.

4 Claims, No Drawings

METHOD OF PRODUCING MONO-SUBSTITUTED TERMINAL DIESTERS

BACKGROUND OF THE INVENTION

This invention relates to a novel process for the production of mono-substituted terminal diesters of malonic acid. These diesters have utility as starting materials and intermediates for the synthesis of pharmacologically active compounds such as the barbituates and related hypnotics, sedatives, tranquilizers and anesthetics.

In 1903 Emil Fischer and J. von Mering synthesized a number of derivatives of barbituric acid by condensing urea with diethyl malonate (commonly called malonic ester) under the influence of sodium ethoxide as a condensing agent. Some of these derivatives were found by these scientists to be valuable as soporifics. The preparation of the lead compound of these 5,5'-disubstituted barbiturates, namely 5,5'-diethylbarbituric acid (Veronal®, barbital), as described in German Patent No. 146,496 (1903), can be illustrated as follows:

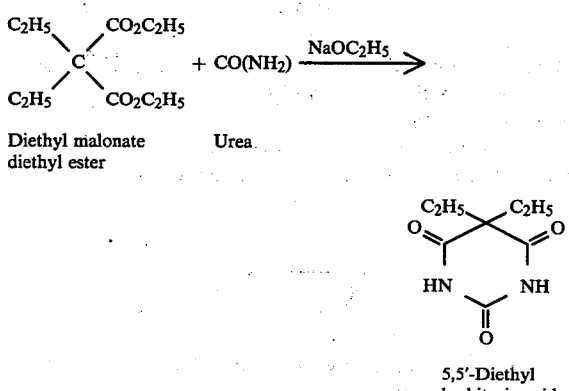

Several hundreds of these barbiturate derivatives having various hypnotic, sedative, tranquilizing and anesthetic activities have since been synthesized. See Blicke and Cox, *Medicinal Chemistry*, Vol. IV, page 1, John Wiley & Sons, New York, 1963. These compounds are especially useful as the sodium salts for absorption from the gastrointestinal tract or for administration through the parenteral route.

The derivatives of barbituric acid now constitute one of the more venerable families of medicinal agents. The aforesaid lead member of the series, barbital, has been in continuous use since its discovery in 1903. The final step in the synthesis of many of the barbiturates consists in either condensation of an organo-substituted malonic or cyanoacetic ester with urea by means of sodium ethoxide or analogous condensation of such an ester with guanidine followed by hydrolysis of the imine thus produced. The chemistry of this class of medicinal agents thus devolves in part on the preparation of suitable organo-substituted malonic acid esters.

Illustrative examples of other well-known members of the barbiturate family of hypnotics and sedatives derived from organo-substituted diesters of malonic acid are as follows:

5-Ethyl-5-phenylbarbiturate, (Luminal®, phenobarbital), can be prepared by the reaction of ethyl phenyl malonate with urea in the presence of sodium ethoxide.

5-Ethyl-5-(1-methylbutyl)barbiturate, (Nembutal®, pentobarbital), can be prepared by the reaction of ethyl-1-methylbutyl malonate in the above reaction system.

5-Allyl-5-(1-methylbutyl)barbiturate, (Seconal®, secobarbital), can be prepared by the reaction of allyl-1-methylbutyl malonate in the same reaction system. See U.S. Patent 1,954,429.

5-Ethyl-5-(1-methylbutyl)-2-thiobarbiturate, (Pentothal®, thiopental), can be prepared condensing ethyl-1-methylbutyl malonate with thiourea in the presence of strong base. This compound is a useful anesthetic agent. See U.S. Pat. No. 2,876,225.

5-Allyl-5-(2-cyclohexen-1-yl)-2-thiobarbituric acid, (Intranarcon®, thialbarbital), can be prepared by condensation of phenyl propenyl malonate with thiourea. The sodium salt is a useful anesthetic agent. See U.S. Pat. No. 2,153,730.

Alkylation of diethyl malonate with a propargyl halide, followed by alkylation with allyl bromide yields the following organo-substituted diester of malonic acid:

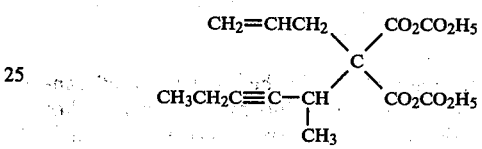

The above diester is a suitable intermediate for the production of 5-allyl-1-methyl-5-(1-methyl-2-pentynyl) barbituric acid, (Brevital®, methohexital), which is a useful anesthetic agent as the sodium salt. See U.S. Pat. No. 2,872,448.

The malonic ester required for the synthesis of the hypnotic and sedative agent, 5-allyl-5-(2-cyclopenten-1-yl) barbituric acid, (Cyclopal®), can be obtained by appropriate alkylation of diethyl allylmalonate

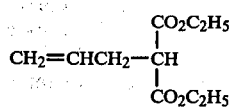

with 1,2-dibromocyclopentane and excess base. See U.S. Pat. No. 1,869,666.

The carbamate sedative, carbamic ester of 5-butyl-5-(2-hydroxyethyl)barbituric acid (Nogexan®, carbubarbital), can be prepared from the intermediate compound diethyl butylmalonate

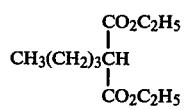

See French Patent No. M1059(1962); British Patent No. 940,533.

The diesters of malonic acid also can be converted to the corresponding glycols which are intermediates for the production of compounds that have found extensive use as drugs to relieve mild anxiety. For example, reduction of malonic ester with lithium aluminum hydride gives the corresponding glycol. Reaction of the glycol with phosgene produces an intermediate which on treatment with ammonia gives the tranquilizer, 2-methyl-2-propyl-1,3-propanediol dicarbamate, (Equanil®, Miltown®, meprobamate), as follows:

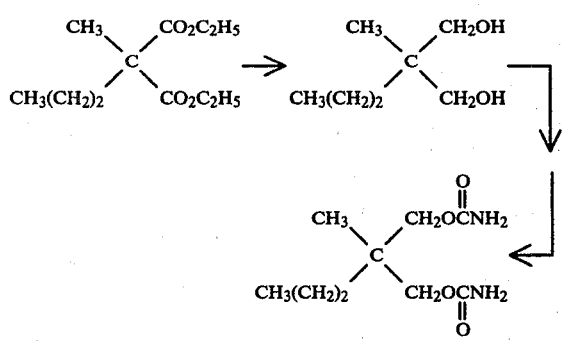

See U.S. Pat. No. 2,724,720.

A similar sequence using another malonic ester,

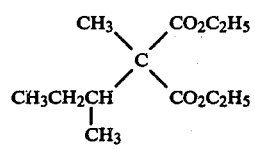

as the starting material, yields the hypnotic and tranquilizer, 2-methyl-2-(1-methylpropyl)-1,3-propanediol dicarbamate, (Butatensin ®, Carbuten ®, mebutamate). See U.S. Pat. No. 2,878,280.

The present invention is directed to a novel method of making terminal diesters of malonic acid of the foregoing general type which can be used as starting materials and intermediates for the production of hypnotics, sedatives, tranquilizers and anesthetics by methods similar to the above illustrative methods.

DESCRIPTION OF THE INVENTION

In accordance with the method of the present invention, mono-substituted terminal diesters of malonic acid are prepared by reaction of the corresponding substituted 1,2-diesters with alkali metal hydride in the presence of organic solvent medium. This novel 1,2-ester transposition reaction can be illustrated by the following general reaction scheme:

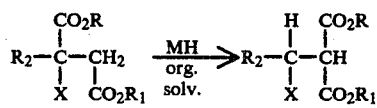

Wherein:
M = Na, K, Li
X = CN, $CO_2R$, $CO_2R_1$
R and $R_1$ = $C_{1-4}$ alkyl
$R_2$ = $C_{1-6}$ alkyl, alkenyl, alkynyl; benzyl and $C_{1-4}$ alkyl substituted benzyl.
Preferably,
R = $R_1$ = $CH_3$, $C_2H_5$
$R_2$ = $CH_3$, $C_2H_5$, benzyl, α-methylbenzyl While investigating the preparation of intermediates for the synthesis of certain pharmaceutical compounds, it was unexpectedly discovered by the present inventors that in both organo-substituted trimethyl ethane-1,1,2-tricarboxylate and organo-substituted dimethyl cyanoethane-1,2-dicarboxylate systems, treatment with alkali metal hydride in organic solvent medium caused an internal ester group to migrate cleanly to the adjacent terminal carbon to give the corresponding organo-substituted dimethyl malonates. Accordingly, the present invention provides a new method for the production of organo-substituted malonic acid diesters which are useful starting materials and intermediates for the production of barbiturates and other such pharmaceutical agents which are known to be synthesized from such diesters.

The inventors are not aware of any 1,2-ester migration reaction having been previously described. However, a 1,3-ester migration, namely the "abnormal" Michael addition, has been reported by Holder and Lapworth, J. Chem. Soc., 2368 (1931).

The invention can be illustrated by the reaction of substituted trimethyl ethane-1,1,2-tricarboxylates and substituted dimethyl cyanoethane-1,2-dicarboxylates with potassium hydride in 1,2-dimethoxyethane (glyme) solvent medium. The unsubstituted tricarboxylate is a known compound described by C. A. Bischoff, Ber. 29 (1), 966–967 (1896), with mp 34.5° C., and has a chemical structure as follows:

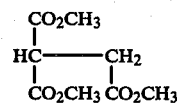

It can be prepared by the reaction of methyl chloroacetate and dimethyl malonate in the presence of sodium methoxide in methanol solvent.

The unsubstituted dicarboxylate has bp 73°–74° C. (1 mm Hg) and a chemical structure as follows:

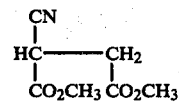

It can be prepared by the reaction of methyl cyanoacetate and methyl chloroacetate in the presence of potassium carbonate in dimethylformamide solvent by procedures analogous to the method for alkylation of methyl 2-cyanopropionate described by D. A. White, Synthetic Comm. 7 (8), 559–568 (1977).

The substituted derivatives of the aforesaid tricarboxylates and dicarboxylates can be obtained by condensation reactions of said carboxylates with the corresponding alkyl, aryl and alkaryl halides such as, for example, methyl iodide, ethyl bromide, benzyl bromide, α-methylbenzyl bromide and the like alkylation compounds.

Treatment of the alkylation adducts of the tricarboxylates and dicarboxylates with KH in glyme leads to the 1,2-ester transposition to provide the corresponding isomers. The resulting terminal malonic acid diesters can then be recovered as essentially pure compounds after acidic workup. (See Examples 1–7, below)

In another example, methyl cyanoacetate can be reacted with acetophenone in the presence of ammonium acetate and acetic acid in refluxing toluene solvent followed by hydrogenation with 5% Pd on C catalyst to yield methyl 2-cyano-3-phenylbutyrate. The latter compound can then be reacted with methyl bromacetate in the presence of potassium carbonate to provide the α-methylbenzyl substituted dimethyl cyanoethane-1,2-dicarboxylate starting 1,2-diester (See Example 8, below):

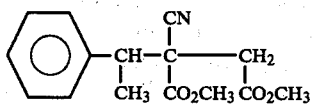

The latter material can then be subjected to the aforesaid 1,2-ester transposition to provide the isomeric terminal diester (See Example 1, below.)

Other alkali metal hydrides such as sodium hydride and lithium hydride can be used in place of the potassium hydride in the 1,2-ester transposition method of the invention. So also, other common organic solvents can be used in place of the glyme, for example, other ethers such as triethylene glycol dimethyl ether (triglyme) and 2-methoxy ethyl ether (diglyme), and other polar solvents such as dimethylsulfoxide (DMSO), dimethylformamide (DMF) and tetrahydrofurane (THF).

The specific illustrative Examples of mono-substituted terminal diesters of malonic acid set forth in the following table were prepared by the foregoing general methods. It will be appreciated, however that the process of the present invention is not limited to these specific examples or to the specific diesters prepared in these examples.

| Example No. | Compound Structure | Molecular Formula | MP* |
|---|---|---|---|
| 1 | Ph—CH(CH₃)—CH(CN)—CH(CO₂CH₃) with CO₂CH₃ | $C_{15}H_{17}NO_4$ | oil |
| 2 | Ph—CH₂—CH(CN)—CH(CO₂CH₃) with CO₂CH₃ | $C_{14}H_{15}NO_4$ | oil |
| 3 | $C_2H_5$CH(CN)—CH(CO₂CH₃) with CO₂CH₃ | $C_9H_{13}NO_4$ | oil |
| 4 | $CH_3$CH(CN)—CH(CO₂CH₃) with CO₂CH₃ | $C_8H_{11}NO_4$ | oil |
| 5 | Ph—CH₂—CH(CO₂CH₃)—CH(CO₂CH₃) with CO₂CH₃ | $C_{15}H_{18}O_6$ | 51–3° C.** |
| 6 | $C_2H_5$—CH(CO₂CH₃)—CH(CO₂CH₃) with CO₂CH₃ | $C_{10}H_{16}O_6$ | oil |
| 7 | $CH_3$—CH(CO₂CH₃)—CH(CO₂CH₃) with CO₂CH₃ | $C_9H_{14}O_6$ | 43–6° C.** |

*Melting points determined on a Reichert hot stage microscope.
**Recrystallized from 30% ethylacetate/petroleum ether.

The structures of the aforesaid rearranged compounds of Examples 1–7 were established by their pmr and mass spectra. $^1$H NMR spectra of deuteriochloroform solutions with tetramethylsilane acting as internal standard ($\delta = 0$ ppm) were taken on Varian T-60 or EM-390 spectrometers. Mass spectral data were obtained with a Finnigan 4000 GC/MS or a Varian CH7A spectrometer. A characteristic pattern of mass fragmentation of the rearranged esters shows the preferential McLafferty rearrangement fragment (e.g., m/e 132 ion) (see F. W. McLafferty, "Interpretation of Mass Spectra", 2d ed., p. 58, W. A. Benjamin, Inc., 1973), while the spectra of the starting materials before the KH treatment indicated the normal cleavage ions. Unambiguous structural evidence for the 1,2-migration was obtained for the reactions with R=CH₃. The pmr spectra of the rearranged products showed 3-hydrogen doublets for the methyl absorption while the pmr spectra of the starting materials were 3-hydrogen singlets.

The 1,1,2-propane tricarboxylic acid trimethyl ester of Example 7 also has been described heretofore as useful for reaction with methyl cinnamate to give stereometric 5-phenyldihydrosarcomycins. Frahm, *Justus Liebigs Ann. Chem.* 1976, 5, 824–34 (German), *Chem. Abstracts* 85, 108327. The sarcomycins are known to be useful as antibiotic and antitumor agents.

Preparation A

General procedure for the preparation of trimethyl 1-alkylethane-1,1,2-tricarboxylate and dimethyl 1-alkyl-1-cyanoethane-1,2-dicarboxylate starting materials for preparation of the compounds of Examples 1–7, above, was as follows:

A mixture of trimethyl ethane-1,1,2-tricarboxylate (for Examples 5–7) or dimethyl 1-cyanoethane-1,2-dicarboxylate (for Examples 1–4), 1.2 equivalent of alkyl halide and 1.5 equivalent of pulverized potassium carbonate in dimethyl sulfoxide was stirred at room temperature. The alkyl halide was α-methylbenzyl bromide for Example 1, benzyl bromide for Examples 2 and 5, ethyl bromide for Examples 3 and 6, and methyl iodide for Examples 4 and 7.

The reaction in each case was monitored by VPC (OV 101 chromatographic column). Ice-water was added after the reaction was completed. To this mixture, cold dilute hydrochloric acid was added until the reaction mixture was neutralized. This mixture was extracted several times with ether, and the combined organic layers were washed sequentially with cold sodium bicarbonate, water and brine, and then dried over magnesium sulfate. The solvent was removed. The desired products were obtained in about 80–88% yields. The products were then used in the KH 1,2-ester transposition reactions of Preparation B, below, without further purification.

PREPARATION B

General procedure for the KH 1,2-ester transposition reaction for the preparation of the compounds of Examples 1–7 was as follows:

An excess amount of KH (35% in oil, 3 mmol) was washed several times with petroleum ether in a three-necked round bottom flask. After removal of petroleum ether, 3 mL of glyme (distilled from calcium hydride and stored over 4A molecular sieves) was added. The reaction mixture (conducted under nitrogen blanket) was stirred at room temperature (ca. 22°–25° C.) for 3 hours. Alternatively, the reaction can be carried out under reflux for about one-half hour. The resulting solution was then cooled in an ice bath before cold water was cautiously added. Workup as described above in the alkylation reactions of Preparation A gave 80–93% yields of essentially pure rearranged products as set forth in Examples 1–7, above.

EXAMPLE 8

Another sample of the starting 1,2-diester of Example 1 was prepared as follows:

A mixture of methyl 2-cyano-3-phenyl butyrate (3.4 g, 0.015 mole), methyl bromacetate (4.5 g, 0.03 mole) and potassium carbonate (3.1 g, 0.023 mole) in 20 mL of dimethylsulfoxide was stirred magnetically for 3 hours. Workup as described in Preparation A, above, afforded a yellow oil which solidified upon standing. Treatment with petroleum ether/ethyl acetate gave 3.1 g of the desired product (75–80% yield) with mp 82.5°–83.5° C.

EXAMPLE 9

Substantially similar results as obtained in the foregoing Examples are obtained when NaH or LiH is substituted for KH and when DMSO, THF, DMF, 2-methoxyethyl ether (diglyme), or triethylene glycol dimethylether (triglyme) is substituted for the glyme solvent.

EXAMPLE 10

When triethyl or tributyl ethane-1,1,2-tricarboxylate is substituted for an equivalent amount of the analogous trimethyl ethane-1,1,2-tricarboxylate and when diethyl or dibutyl 1-cyanoethane-1,2-dicarboxylate is substituted for an equivalent amount of the dimethyl 1-cyanoethane-1,2-dicarboxylate in the foregoing Examples, the corresponding mono-substituted diethyl and dibutyl malonate esters are obtained.

Various other examples will be apparent to the person skilled in the art after reading the present disclosure without departing from the spirit and scope of the invention and it is intended that all such further examples be included within the scope of the invention.

What is claimed is:

1. A method for the preparation of mono-substituted terminal diesters of malonic acid having the structure

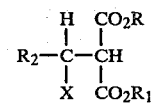

comprising reacting the corresponding substituted 1,2-diesters of the structure

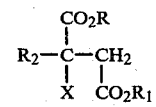

with alkali metal hydride in the presence of organic solvent medium, wherein:

alkali metal = Na, K, Li;

X = CN, $CO_2R$, $CO_2R_1$;

R and $R_1$ = $C_{1-4}$ alkyl;

$R_2$ = $C_{1-6}$ alkyl, alkenyl, alkynyl; benzyl and $C_{1-4}$ alkyl substituted benzyl.

2. The method of claim 1 wherein: R = $R_1$ = $CH_3$, $C_2H_5$.

3. The method of claim 1 wherein the alkali metal hydride is KH.

4. The method of claim 1 wherein the organic solvent medium is 1,2-dimethoxyethane.

* * * * *